United States Patent [19]

Beck

[11] Patent Number: 4,956,349

[45] Date of Patent: Sep. 11, 1990

[54] ANTI-INFLAMMATORY FACTOR, METHOD OF ISOLATION, AND USE

[75] Inventor: Lee R. Beck, Lebanon, Ohio

[73] Assignee: Stolle Research & Development Corporation, Lebanon, Ohio

[21] Appl. No.: 177,223

[22] Filed: Apr. 4, 1988

Related U.S. Application Data

[60] Continuation-in-part of Ser. No. 1,848, Jan. 9, 1987, Pat. No. 4,897,265, which is a continuation-in-part of Ser. No. 384,625, Jun. 3, 1982, abandoned, which is a division of Ser. No. 546,162, Oct. 27, 1983, Pat. No. 4,636,384, which is a division of Ser. No. 910,297, Sep. 17, 1986, which is a continuation of Ser. No. 576,001, Feb. 1, 1983, abandoned.

[51] Int. Cl.$^5$ ................... A61K 31/715; A61K 35/20; C08B 37/00
[52] U.S. Cl. ........................................ 514/54; 536/1.1; 536/24; 424/85.8; 424/92; 424/535
[58] Field of Search ................... 424/85.8, 92, 95; 514/2 B, 54; 536/1.1, 24

[56] References Cited

U.S. PATENT DOCUMENTS

| | | | |
|---|---|---|---|
| 3,128,230 | 4/1964 | Heinbach | 167/78 |
| 3,376,198 | 4/1968 | Peterson et al. | 167/78 |
| 4,284,623 | 8/1981 | Beck | 424/85 |
| 4,324,782 | 4/1982 | Beck | 424/87 |
| 4,402,938 | 9/1983 | Collins et al. | 426/583 |
| 4,636,384 | 1/1987 | Stolle et al. | 424/87 |
| 4,732,757 | 3/1988 | Stolle et al. | 424/87 |

FOREIGN PATENT DOCUMENTS 1211876 11/1970 United Kingdom.
1442283 7/1976 United Kingdom.

*Primary Examiner*—Blondel Hazel
*Attorney, Agent, or Firm*—Saidman, Sterne, Kessler & Goldstein

[57] ABSTRACT

The invention relates to a substantially pure antiinflammatory factor isolated from milk collected from a milk producing animal, to the purification, identification, and characterization of said factor, and to a method for treating inflammation in an animal which comprises administering to the animal an anti-inflammatorily effective amount of the anti-inflammatory factor. In a preferred embodiment, the factor is isolated from milk is produced by a milk producing animal maintained in a hyperimmunized state.

23 Claims, 2 Drawing Sheets

ANTI-INFLAMMATORY FACTOR, METHOD OF ISOLATION, AND USE

This application is a continuation-in-part, of U.S. Ser. No. 001,848, filed Jan. 9, 1987 now U.S. Pat. No. 4,897,265, which is a continuation-in-part of U.S. Ser. No. 384,625, filed June 3, 1982, now abandoned, and a division of U.S. Ser. No. 546,162, filed Oct. 27, 1983 now U.S. Pat. No. 4,636,384 and of U.S. Ser. No. 910,297, filed Sep. 17, 1986, which is a file wrapper continuation of U.S. Ser. No. 576,001, filed Feb. 1, 1983.

BACKGROUND OF THE INVENTION

1. Field of the Invention

The present invention relates to an anti-inflammatory factor (AF), a process for its production in substantially pure form, and a method for its use in the treatment of inflammation.

2. Description of the Background Art

Inflammation, as defined in Dorland's Medical Dictionary, is "a localized protective response elicited by injury or destruction of tissues which serves to destroy, dilute or wall off both the injurious agent and the injured tissue." It is characterized by fenestration of the microvasculature, leakages of the elements of blood into the interstitial spaces, and migration of leukocytes into the inflamed tissue. On a macroscopic level, this is usually accompanied by the familiar clinical signs of erythema, edema, tenderness (hyperalgesia), and pain. During this complex response, chemical mediators such as histamine, 5-hydroxytryptamine, various chemotactic factors, bradykinin, leukotrienes, and prostaglandins are liberated locally. Phagocytic cells migrate into the area, and cellular lysosomal membranes may be ruptured, releasing lytic enzymes. All of these events may contribute to the inflammatory response.

Inflammation in patients with rheumatoid arthritis probably involves the combination of an antigen (gamma globulin) with an antibody (rheumatoid factor) and complement causing the local release of chemotactic factors that attract leukocytes. The leukocytes phagocytose the complexes of antigen-antibody and complement and also release the many enzymes contained in their lysosomes. These lysosomal enzymes then cause injury to cartilage and other tissues, and this furthers the degree of inflammation. Cell-mediated immune reactions may also be involved. Prostaglandins are also released during this process.

Prostaglandins, which are likely to be generated in inflammation, cause erythema and increase local blood flow. Two important vascular effects of prostaglandins are not generally shared by other mediators of inflammation—a long-lasting vasodilator action and a capacity to counteract the vasoconstrictor effects of substances such as norepinephrine and angiotensin.

A number of mediators of inflammation increase vascular permeability (leakage) in the post-capillary and collecting venules. In addition, migration of leukocytes into an inflamed area is an important aspect of the inflammatory process. While prostaglandins are unlikely to be directly involved in the chemotactic response, another product of the metabolism of arachidonic acid, leukotriene, is a very potent chemotactic substance.

The anti-inflammatory response is any response characterized by inflammation as defined above. It is well known to those skilled in the medical arts that the inflammatory response causes much of the physical discomfort, i.e., pain and loss of function, that has come to be associated with different diseases and injuries. Accordingly, it is a common medical practice to administer pharmacological agents which have the effect of neutralizing the inflammatory response. Agents having these properties are classified as anti-inflammatory drugs. Anti-inflammatory drugs are used for the treatment of a wide spectrum of disorders, and the same drugs are often used to treat different diseases. Treatment with anti-inflammatory drugs is not for the disease, but most often for the symptom, i.e., inflammation.

The anti-inflammatory, analgesic, and anti-pyretic drugs are a heterogeneous group of compounds, often chemically unrelated, which nevertheless share certain therapeutic actions and side-effects. Corticosteroids represent the most widely used class of compounds for the treatment of the anti-inflammatory response. Proteolytic enzymes represent another class of compounds which are claimed to have anti-inflammatory effects. Hormones which directly or indirectly cause the adrenal cortex to produce and secrete steroids represent another class of anti-inflammatory compounds. A number of nonhormonal anti-inflammatory agents have been described. Among these, the most widely used are the salicylates. Acetylsalicylic acid, or aspirin, is the most widely prescribed analgesic-antipyretic and anti-inflammatory agent. Examples of steroidal and non-steroidal anti-inflammatory agents are listed in the *Physician's Desk Reference*, 1987 (see pp. 207 and 208 for an index of such preparations).

The natural and synthetic corticosteroid preparations cause a number of severe side effects, including elevation of blood pressure, salt and water retention, and increased potassium and calcium excretion. Moreover, corticosteroids may mask the signs of infection and enhance dissemination of infectious microorganisms. These hormones are not considered safe for use in pregnant women, and long-term corticosteroid treatment has been associated with gastric hyperactivity and/or peptic ulcers. Treatment with these compounds may also aggravate diabetes mellitus, requiring higher doses of insulin, and may produce psychotic disorders. Hormonal anti-inflammatory agents which indirectly increase the production of endogenous corticosteroids have the same potential for adverse side-effects.

The non-hormonal anti-inflammatory agents are synthetic biochemical compounds which can be toxic at high doses with a wide spectrum of undesirable side-effects. For example, salicylates contribute to the serious acid-base balance disturbances that characterize poisoning by this class of compounds. Salicylates stimulate respiration directly and indirectly. Toxic doses of salicylates cause central respiratory paralysis as well as circulatory collapse secondary to vasomotor depression. The ingestion of salicylate may result in epigastric distress, nausea, and vomiting. Salicylate-induced gastric bleeding is well known. Salicylates can produce hepatic injury, and lead to a prolongation of clotting time. Therefore, aspirin should be avoided in patients with severe hepatic damage, hypoprothrombinemia, vitamin K deficiency, or hemophilia, because the inhibition of platelet hemostasis by salicylates can result in hemorrhage. Salicylate intoxication is common, and over 10,000 cases of serious salicylate intoxication are seen in the United States every year, some of them being fatal, and many occurring in children. See Goodman and Gilman's *The Pharmacological Basis of Therapeutics*, 7th Ed., 1985. Accordingly, in spite of the large number of anti-inflammatory agents that are currently available, there still exists a need for a safe, effective anti-inflammatory product which is free of side-effects and adverse reactions.

If a natural food product, such as one derived from milk, for example, could be obtained having anti-inflammatory effects, it would be an easily administrable, readily available, safe therapeutic composition.

It has been known in the prior art to produce milks having a variety of therapeutic effects. Beck, for example, has disclosed a milk containing antibody to *Streptococcus mutans* that has dental caries inhibiting effect (U.S. Pat. No. 4,324,782). The milk is obtained by immunizing a cow with *S. mutans* antigen in two stages and obtaining the therapeutic milk therefrom.

Stolle et al. have disclosed a method for treating vascular disorders or pulmonary disorders associated with smoking in an animal which comprises administering to the animal milk collected from a cow being maintained in a hyperimmune state (U.S. Patent No. 4,636,384). Beck has disclosed a method for treating inflammation in an animal which comprises administering to the animal an anti-inflammatory effective amount of milk collected from a cow maintained in an anti-inflammatory factor producing state (U.S. Pat. No. 4,284,623). Heinbach, U.S. Pat. No. 3,128,230, has described milk containing globulins of alpha, beta, and gamma components by inoculating a cow with antigenic mixtures. Peterson et al. (U.S. Pat. No. 3,376,198), Holm (U.S. Application (published) Ser. No. 628,987), Tunnah et al. (British Patent No. 1,211,876) and Biokema S.A. (British Patent No. 1,442,283) have also described antibody-containing milks.

None of the aforementioned references, however, disclose the identity of the component or components of therapeutic milks which produce the desired therapeutic effects. For example, in Beck, U.S. Pat. No. 4,284,623, the milk products used as a therapeutic means consist of either fluid whole milk, fluid fat-free whey, or whole milk powders. Although each of these milk products has anti-inflammatory properties, the factor or factors that actually provide the therapeutic benefits have not yet been isolated or identified.

SUMMARY OF THE INVENTION

The present invention is based upon the inventor's consideration that an isolated and purified anti-inflammatory milk product would be most useful to treat anti-inflammatory disorders in an animal.

With this in mind, the present inventors isolated and partially purified and characterized an anti-inflammatory factor from hyperimmune bovid milk, hereinafter called milk anti-inflammatory factor (MAIF).

Further investigation demonstrated that this milk product prevented or alleviated the clinical symptoms of inflammation. Accordingly, the present invention is the discovery that anti-inflammatory factor, isolated from milk from milk-producing animals previously hyperimmunized against particular polyvalent antigens, is effective against inflammatory conditions when said isolated and purified anti-inflammatory factor is administered in an amount and under a regimen sufficient to produce anti-inflammatory effects. This discovery is particularly surprising in view of the fact that the polyvalent antigen vaccine itself does not contain MAIF. The isolation of the active factor from milk of hyperimmunized bovines led to the unexpected finding that the MAIF occur in small quantities in the milk of normal bovines. This discovery had been hidden by the fact that the concentration of MAIF in normal bovine milk is too low to confer discernible anti-inflammatory properties to the milk. The MAIF of normal milk can, however, be concentrated by the isolation process of the invention, and thereafter can be used effectively to treat inflammation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
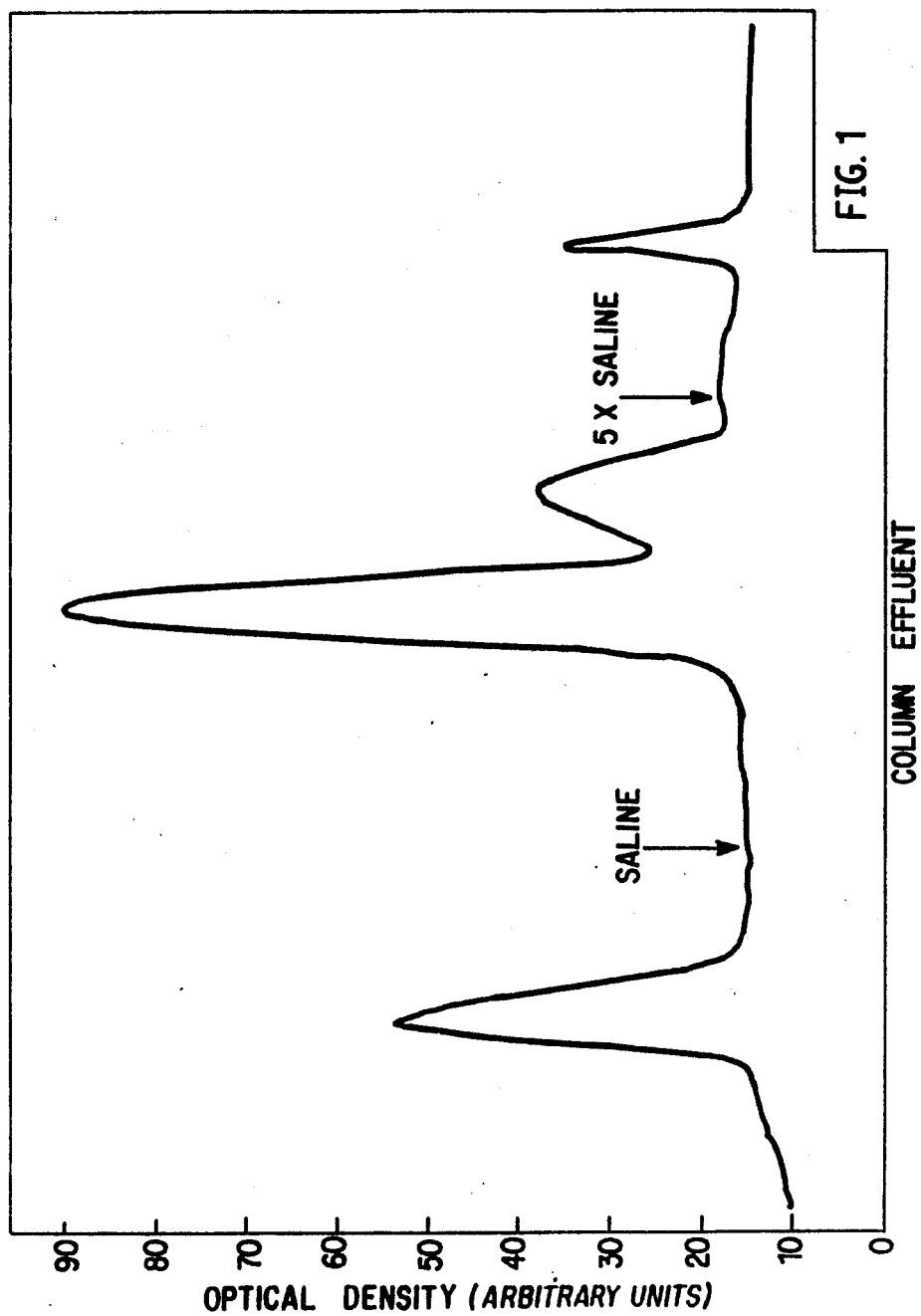
FIG. 1. Isolation of MAIF b ion-exchange chromatography on a column of DEAE-cellulose, in Step 2 of the preferred process.

The invention comprises the isolation and purification of MAIF and the administration of said MAIF to an animal for the purpose of treating anti-inflammatory disorders.

By the term "milk anti-inflammatory factor (MAIF)" is intended a factor obtained from either hyperimmune milk or normal cow's milk. By the term "substantially pure MAIF" is intended, for the purpose of this invention, an anti-inflammatory factor that elutes as a single major symmetrical peak on HPLC chromatography, after removal of high molecular weight substances ($>10,000$ daltons) and isolation of the low molecular weight, negatively-charged species by ion-exchange chromatography. Both normal milk and hyperimmune milk can be processed by the methods described herein to obtain the MAIF.

By the term "hyperimmune milk" is intended, for the purpose of this invention, milk obtained from milk-producing animals maintained in a hyperimmune state, the details for hyperimmunization being described in greater detail below.

By the term skimmed milk is intended, for the purpose of this invention, milk from which cream has been removed.

By the term "normal milk" is intended for the purpose of the invention milk that is obtained from milk-producing animals by conventional means and dairy practices.

By the term "milk-producing animal" is intended, for the purpose of this invention, mammals that produce milk in commercially feasible quantities, preferably cows, sheep and goats, more preferably dairy cows of the genus Bos (bovid), particularly those breeds giving the highest yields of milk, such as Holstein.

By the term "bacterial antigen" is intended, for the purpose of this invention, a lyophilized preparation of heat-killed bacterial cells.

By the term "microencapsulated form" is intended, for the purpose of this invention, polymeric microparticles encapsulating one or more bacterial antigens for administration to milk-producing animals.

By the term "inflammation" is intended, for the purpose of this invention, a localized protective response elicited by injury or destruction of tissues which serves to destroy, dilute or wall off both the injurious agent and the injured tissue, characterized in the acute form by the classical sequence of pain, heat, redness, swelling, and loss of function, and histologically involving a complex series of events, including dilatation of the arterioles, capillaries, and venules with increased permeability and blood flow, exudation of fluids including plasma proteins, and leukocyte migration into the inflammatory focus.

By the term "treating" is intended, for the purposes of this invention, that the symptoms of the disorder and/or pathogenic origin of the disorder be ameliorated or completely eliminated.

By the term "administer" is intended, for the purpose of this invention, any method of treating a subject with a substance, such as orally, intranasally, parenterally (intravenously, intramuscularly, or subcutaneously), or rectally.

By the term "animal" is intended, for the purpose of this invention, any living creature that is subject to inflammation, including humans, farm animals, domestic animals, or zoological garden animals.

Examples of inflammatory conditions that may be treated by the isolated and purified milk product of the present invention are conditions selected from the group consisting of acute and subacute bursitis, acute nonspecific tendonitis, systemic lupus erythematosis, systemic dermatomyositis, acute rheumatic carditis, pemphigus, bullous dermatitis, herpeteformis, severe erythema, multiform exfoliative dermatitis, cirrhosis, seasonal perennial rhinitis, bronchial asthma, ectopic dermatitis, serum sickness, keratitis, opthalmicus iritis, diffuse ureitis, choriditis, optic neuritis, sympathetic opthalmia, symptomatic sarcoidosis, Loeffler's syndrome, berylliosis, hemolytic anemia, mastitis, mastoiditis, contact dermatitis, allergic conjunctivitis, psoriatic arthritis, ankylosing spondylitis, acute gouty arthritis, and herpes zoster. Further, the isolated and purified milk product may be used to treat individuals who are exposed to potentially inflammatory agents.

The invention is based in part on the discovery that when a milk-producing animal such as a bovid is brought to a specific state of hyperimmunization, the animal will produce milk which has supranormal levels of the highly beneficial MAIF, said MAIF not only suppressing the symptoms of inflammation in man and other animals, but also being a prophylactic agent in anticipation of the presence of inflammatory agents in the recipient. By the term "supranormal levels" is intended levels in excess of that found in milk from non-hyperimmunized animals. The induction of immune sensitivity alone is insufficient to cause the appearance of supranormal levels of MAIF in milk, as is shown by the fact that normal cow's milk does not contain these supranormal levels, even though the cows have become sensitized against various antigens during normal immunization against cow diseases and during normal exposure to the environment. It is only in specific hyperimmune states that the milk has the desired supranormal levels.

This special state may be achieved by administering an initial immunization, followed by periodic boosters with sufficiently high doses of specific antigens. The preferred dosage of booster should be equal to or greater than 50% of the dosage necessary to produce primary immunization of the bovid. Thus, there is a threshold booster dosage below which the properties are not produced in the milk, even though the cow is in what normally would be called an immune state. In order to achieve the requisite hyperimmune state, it is essential to test the hyperimmune milk after a first series of booster administrations. If the beneficial factors are not present in the milk, additional boosters of high dosage are administered until the properties appear in the milk.

The process of producing the hyperimmune milk containing supranormal levels of MAIF is disclosed in co-pending U.S. Ser. Nos. 069,139, filed July 2, 1987, and 910,297, filed Sept. 17, 1986, a file wrapper continuation of U.S. patent application Ser. No. 576,001, filed Feb. 1, 1983, which are incorporated herein by reference. In summary, one process of producing the hyperimmune milk containing supranormal levels of MAIF comprises the following steps: (1) antigen selection; (2) primary immunization of the bovid; (3) testing the serum to confirm sensitivity induction; (4) hyperimmunization with boosters of appropriate dosage; and, optionally, (5) testing the milk for anti-inflammatory properties; (6) collecting the milk from the hyperimmune bovid; and (7) processing the milk to isolate the MAIF.

Step 1: Any antigens or combination of antigens may be employed. The antigens can be bacterial, viral, protozoan, fungal, cellular, or any other substances to which the immune system of a milk-producing animal will respond. The critical point in this step is that the antigen(s) must be capable, not only of inducing immune and hyperimmune states in the milk-producing animal, but also of producing supranormal levels of MAIF in the milk. Any antigen can be used to produce supranormal levels of MAIF. One preferred vaccine is a mixture of polyvalent bacterial antigens, referred to as Series 100 vaccine, described in detail in Example 1A below.

Step 2: The antigen(s) can be administered in any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, rectal suppository, or oral administration may be used.

Step 3: It is necessary to determine whether or not the milk-producing animal has become sensitive to the antigen. There are a number of methods known to those skilled in the art of immunology to test for sensitivity (*Methods in Immunology and Immunochemistry*, William, C. A., and Chase, W. M., Academic Press, New York, vols. 1–5 (1975)). The preferred method is to use a polyvalent vaccine comprising multiple bacterial species as the antigen and to test for the presence of agglutinating antibodies in the serum of the animal before and after challenge with the vaccine. The appearance of milk antibodies after immunization with the vaccine indicates sensitivity; at this point it is possible to proceed to step 4.

Step 4: This involves the induction and maintenance of the hyperimmune state in the sensitized animal. This is accomplished by repeated booster administration at fixed time intervals of the same polyvalent vaccine that was used to achieve the primary sensitization. A two-week booster interval is optimal for polyvalent bacterial antigens. However, it is necessary to ensure that the animal does not pass from a hyperimmune state to a state of immune tolerance to the antigen.

In a preferred embodiment, hyperimmunization of bovids may be achieved by a single administration of microencapsulated vaccine, prepared as described in detail in Example IB below. The advantage of the controlled release form of hyperimmunization is that the constant exposure to the antigen ensures that the animal remains in the hyperimmune state.

In an alternative embodiment, it is also possible to combine different immunization procedures, e.g., simultaneously administering microencapsulated and liquid antigen, or intramuscular injection for primary immunization, and booster doses by oral administration or parenteral administration by microencapsulation means. Many different combinations of primary and hyperimmunization are known to those skilled in the art.

Step 5: It is necessary to test the milk for anti-inflammatory activity levels. This can be accomplished by any research technique that tests the effects of either the hyperimmune milk or products derived therefrom upon inflammation. Chemical-induced inflammation of the rat paw is a standard assay for anti-inflammatory drugs.

Step 6: This involves the collection and processing of the milk. The milk can be collected by conventional methods. Processing the milk to isolate the MAIF is described below.

The simplest process for isolating, purifying and testing the MAIF comprises the following steps:

1. defatting the hyperimmune milk to produce skim milk;
2. removing casein from skim milk to produce whey;
3. removal from the whey macromolecules of molecular weight greater than about 10,000 daltons by ultrafiltration;
4. fractionating the product from step 3 using an ion-exchange resin column to isolate a negatively-charged MAIF species of molecular weight less than about 10,000 daltons;
5. separating the negatively-charged species from step 4 by molecular sieve chromatography; and
6. biological assay of MAIF from step 5.
7. The anti-inflammatory action of the milk factor is tested on edema that is caused by the injection of a solution of carrageenan into the paw of rats. The rat paw test is the standard animal test for anti-inflammatory drugs. Winter, C. A., Risley, G. A., Nuss, A. W., "Carrageenin-Induced Edema in the Hind Paw of the Rat as an Assay for Anti-inflammatory Drugs," *Proc. Soc. Exper. Biol. Med.* 3:544 (1967). A variety of other tests may be used. Wetnick, A. S., and Sabin, C., "The Effects of Clonixin and Bethaurethasone on Adjuvant-Induced Arthritis and Experimental Allergic Encephalomyelitis in Rats," *Jap. J. Pharm.* 22:741 (1972). However, the rat paw test is the most simple and direct test available, and has been shown to be satisfactory for all anti-inflammatory drugs. This test has been described in detail in Beck, U.S. Pat. No. 4,284,623, which is incorporated herein by reference to the extent that it describes the rat paw test. Briefly, the test involves the injection of a small quantity of carrageenin into the footpad of adult white rats. This is known to induce an inflammatory response. The resulting degree of swelling can be quantified. Samples containing an AF (anti-inflammatory factor) are administered to the rat by a suitable route, preferably by intraperitoneal injection, and the blockade or amelioration of the inflammatory process quantified by either volumetric or gravimetric methods.

In summary, one can isolate the anti-inflammatory factor from hyperimmunized milk by following a process of defatting the milk, removing casein, removing macromolecules of greater than 10,000 daltons, and continuing with ion exchange and molecular sieve chromatography. The biological activity of appropriate preparations of anti-inflammatory factor can be tested by doing a dose-response experiment on rats as described herein.

The invention is based in part upon the unexpected discovery that a MAIF can be isolated and purified and is effective in treating a variety of inflammatory processes in humans and animals. In a preferred embodiment, the MAIF is produced by hyperimmunizing a milk-producing animal against a bacterial antigen vaccine. The vaccine used to hyperimmunize the animals does not contain anti-inflammatory activity. It is surprising, therefore, that treatment with an isolated and purified factor, obtained from animals immunized against a mixed bacterial antigen vaccine, is effective in alleviating or eliminating inflammatory processes.

Having now described the invention in general terms, the same will be further described by reference to certain specific examples that are provided herein for purposes of explanation only, and are not intended to be limiting unless otherwise specified.

PREPARATION OF MILKS

Example 1A

Preparation of S-100 Vaccine

A bacterial culture containing the spectrum of bacteria shown in Table 1 below as obtained from the American Type Culture Collection was reconstituted with 15 ml of media and incubated overnight at 37° C. Once good growth was obtained, approximately one-half of the bacterial suspension was employed to inoculate one liter of broth with the inoculate being incubated at 37° C. The remaining suspension was transferred to sterile glycol tubes and stored at −20° C. for up to six months.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet obtained upon centrifugation was resuspended in a small amount of double distilled water.

The media-free bacterial suspension was heat-killed by placing the suspension in a glass flask in an 80° C. water bath overnight. The viability of the broth culture was tested with a small amount of heat-killed bacteria. Broth was inoculated with heat-killed bacteria, incubated at 37° C. for five days and checked daily for growth, as the bacteria have to be killed for use in the vaccine.

The heat-killed bacteria were lyophilized until dry. The dry bacteria were then mixed with sterile saline solution to a concentration of $2.2 \times 10^8$ bacterial cells/ml saline (1.0 optical density reading at 660 nm.)

TABLE 1
S-100 Bacteria List

| Name | Media | Gram + or − | ATTC # |
|---|---|---|---|
| 1. Staph. aureus | BHI | + | 11631 |
| 2. Staph. epidermidis | BHI | + | 155 |
| 3. Strep. pyogenes, A. Type 1 | APT | + | 8671 |
| 4. Strep. pyogenes, A. Type 3 | APT | + | 10389 |
| 5. Strep. pyogenes, A. Type 5 | APT | + | 12347 |
| 6. Strep. pyogenes, A. Type 8 | APT | + | 12349 |
| 7. Strep. pyogenes, A. Type 12 | APT | + | 11434 |
| 8. Strep. pyogenes, A. Type 14 | APT | + | 12972 |
| 9. Strep. pyogenes, A. Type 18 | APT | + | 12357 |
| 10. Strep. pyogenes, A. Type 22 | APT | + | 10403 |
| 11. Aerobacter aerogenes | BHI | − | 884 |
| 12. Escherichia coli | BHI | − | 26 |
| 13. Salmonella enteritidis | BHI | − | 13076 |
| 14. Pseudomonas aeruginosa | BHI | − | 7700 |
| 15. Klebsiella pneumoniae | BHI | − | 9590 |
| 16. Salmonella typhimurium | BHI | − | 13311 |
| 17. Haemophilus influenzae | BHI | − | 9333 |
| 18. Strep. mitis | APT | + | 6249 |
| 19. Proteus vulgaris | BHI | − | 13315 |
| 20. Shigella dysenteriae | BHI | − | 11835 |
| 21. Diplococcus pneumoniae | APT | + | 6303 |
| 22. Propionibacter acnes Actinomyces (anaerobe) | Broth | + | 11827 |
| 23. Strep. sanguis | APT | + | 10556 |
| 24. Strep. salivarius | APT | + | 13419 |
| 25. Strep. mutans | BHI | + | 25175 |
| 26. Strep. agalactiae | APT | + | 13813 |

Cows were given daily injections of 5 ml samples of the polyvalent liquid vaccine. Antibody (IgG) titer levels for the injected cattle were determined periodically by using an enzyme-linked immunoassay for bovine antibody against the polyvalent antigen.

EXAMPLE 1B

Heat-killed bacteria were prepared in the manner described above. The polyvalent antigen sample (S-100) obtained was microencapsulated by a conventional phase-separation process to prepare a polyvalent antigen-containing microparticle product. Generally, the antigen-containing shaped matrix materials are formed from polymers of biocompatible material, preferably biodegradable or bioerodable materials, preferably polylactic acid, polyglycolic acid, copolymers of lactic and glycolic acids, polycaptolactone, copolyoxalates, proteins such as collagen, fatty acid esters of glycerol, and cellulose esters. These polymers are well known in the art and are described, for example, in U.S. Pat. Nos. 3,773,919; 3,887,699; 4,118,470; 4,076,798; all incorporated by reference herein. The polymeric matrix material employed was a biodegradable lactide-glycolide copolymer.

Heat-killed bacterial antigens are encapsulated in such matrix materials, preferably as microspheres of between 1-500 microns diameter, preferably 10-250 microns. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The microparticles in the example were less than 250 microns in diameter. Approximately 750 mg of microparticles containing 22% (16.5 mg) of polyvalent antigen was then suspended in about 3 cc of a vehicle (1 wt % Tween 20 and 2 wt % carboxymethyl cellulose in water).

A small group of cattle was selected from a larger herd of cattle. Five of these randomly selected cattle were selected as controls. Four cattle were injected intramuscularly with microparticles containing polyvalent antigen. Microparticle samples were sterilized with 2.0 mRad of gamma radiation. Antibody (IgG) titer levels were determined periodically from samples of cows' milk obtained from the inoculated cows, as well as from the control cows.

EXAMPLE 2

Isolation of MAIF Factor from Hyperimmunized Milk

Step 1: Milk Filtrate Preparation

Twenty liters of fresh milk from hyperimmunized cows were run through a cream separator (DeLaval Model 102) to remove the fat.

The resulting sixteen liters of skimmed milk was ultra-filtered to remove the high molecular weight species (over 10,000 daltons) using a hollow fiber diafiltration/concentrator (Amicon DL-10L). The concentrator is equipped with two 10,000 daltons molecular weight cut-off cartridges (Amicon $H_5P_{10-43}$). The skimmed milk was run at the pump speed of 80 on the meter and inlet and outlet pressure of 30 psi and 25 respectively.

Twelve liters of the filtrate (<10,000 daltons) coming out of the cartridges at the flow rate of four liters per hour was frozen or lyophilized for storage and for further purification.

Step 2: Ion-Exchange Chromatography

The milk anti-inflammatory factor, MAIF, in the filtrate was first isolated by an anion exchange chromatography column.

In this procedure, DEAE-Sepharose CL-6B gel (Pharmacia) was used to pack a 5×10 cm glass column which was equilibrated with sterile double distilled water, pH 7.0.

One liter of filtrate (<10,000) was applied to the column and eluted with sterile double distilled water, pH 7.0 at the flow rate of 160 ml per hour. Ten milliliter fractions were collected and monitored at 280 nm in an LKB Uvicord 4700 absorptiometer with an optical density printed out on a connected recorder (Pharmacia REC-482).

The substances other than MAIF having positive and neutral charges are not bound to the DEAE-Sepharose gel. They are eluted at the fallthrough peak (first peak). The MAIF carrying a negative charge is retained by the gel.

To discharge the MAIF, the column was eluted with a stepwise gradient using sterile physiological saline, pH 7.0. A typical profile is shown in FIG. 1. Bioassay of the individual fractions revealed that the second peak contains the MAIF. Fractions comprising the second peak and its shoulder are used for further purification. Recovery studies show that 8.8 grams of dried powder were obtained by this process.

Step 3: Gel Filtration Chromatography

The second peak obtained from Step 2 contains MAIF and other negatively charged molecules; therefore, an additional refining step was needed. To achieve further purification, it is convenient to use a gel filtration column to separate various components on the basis of molecular weight.

In this process, Sephadex G-10 resin (Pharmacia) was packed into a 2.5×80 cm glass column and equilibrated with sterile double distilled water, pH 7.0. Two grams of the second fraction from Step 2 was redissolved in sterile double distilled water and applied to the top of the column. The column was eluted at the flow rate of 30 ml per hour. Fractions (3.3 ml) were collected and monitored at 254 nm and 280 nm (Pharmacia Duo Optical Unit) with optical density printed out on a connected recorder (Pharmacia REC-482).

Figure 2:
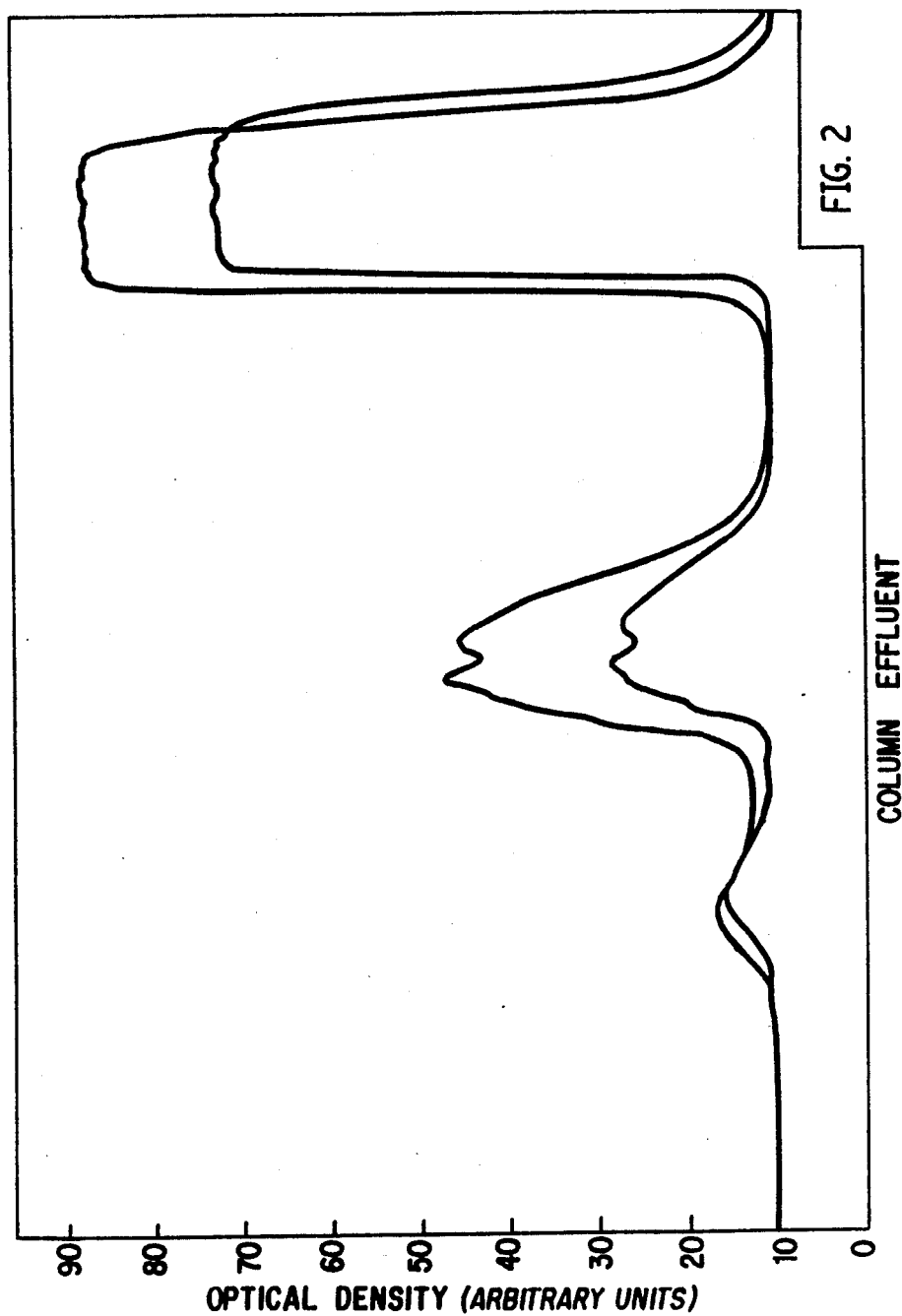
FIG. 2. Fractionation of the MAIF peak (second) from DEAE-cellulose chromatography (FIG. 1) on a Sephadex G-10 molecular sieve column, in step 3 of the preferred process.

Typically, there were 3 peaks shown in the elution profile as illustrated in FIG. 2. The first and second peaks contained MAIF activity.

The first peak is an aggregate that forms on the G-10 column which contains the active MAIF.

The second peak contains the nonaggregated form of the MAIF. Both the aggregate form (peak 1) and the nonaggregated form (peak 2) are biologically active in rat bioassay.

CHARACTERIZATION OF MILK ANTI-INFLAMMATORY FACTOR

The molecular weight of the non-aggregated form of MAIF prepared by the method described above was found to be less than 10,000 daltons. This was deduced from the fact that the first step in the isolation of MAIF from whey was by ultrafiltration using a membrane that does not allow the passage of molecular weight species >10,000 daltons.

The MAIF has a negative charge. This was determined by applying milk ultrafiltrate to a DEAE cellulose ion exchange column. The MAIF did not elute from the column with water. Changing the elution media to sodium chloride (0.9% pH) caused the elution of several peaks (FIG. 1). Neutral and positive charged species do not adhere to the ion exchange resin, and negative charged species are eluted by increasing the salt concentration. When the less than 10,000 dalton molecular weight permeate was applied to the DEAE column, neutral salts and sugars eluted with water (Peak 1, FIG. 1). Three distinct peaks eluted when the buffer was changed to saline (Peaks 2-4). The second peak and its shoulder contained MAIF biological activity in the rat assay. It is concluded, therefore, that the MAIF has a negative charge.

Another chemical characteristic of the MAIF is that it forms an aggregate during the process of removing salt. This property becomes apparent when <10,000 dalton molecular weight permeate was passed over a Sephadex G-10 column, equilibrated with double distilled water and eluted with water at a pH of 7 (FIG. 2). Three peaks eluted from the G-10 column; the first peak eluted with the void volume suggesting a molecular weight equal to or greater than 10,000 dalton. This was unexpected because molecules greater than 10,000 daltons had previously been removed from this sample by ultrafiltration. The second peak eluted in the position expected for the anti-inflammatory factor. Both the first and second peaks exhibited anti-inflammatory biological activity in the rat paw assay, whereas the third peak lacked activity. It was surprising to find that both the first and second peaks had anti-inflammatory biological activity. The material recovered from the first peak of the G-10 column (Step 3) was lyophilized and applied to a G-100 column; a single peak was eluted with the void volume, suggesting a molecular weight of 100,000 daltons or greater. The Step 3 G-10 column removes salt at the same time it separates the different molecular weight species. It is concluded, therefore, that during passage over the G-10 column and resulting removal of salt the anti-inflammatory factor formed a large molecular weight aggregate. The degree of aggregation varied with the salt concentration.

The aggregation property suggests the possibility that a wide spectrum of different molecular weight species can be formed which have anti-inflammatory biological activity due to the presence of the anti-inflammatory factor. The discovery of this property suggests the possibility of producing milk anti-inflammatory factors having a wide spectrum of different biochemical properties depending on the degree of aggregation of the final product. For example, formulations having longer or shorter biological half lives might be produced by using larger or smaller molecular weight aggregates, with molecular weight distribution being controlled by the salt concentration during processing. The column chromatography method described herein results in the smallest molecular weight species that has been obtained which has biological activity (i.e., peak 2 from the Step 3 G-10 column). This observation also suggests using other methods for forming the aggregates. For example, dilution in water causes the aggregation to occur. Chemical agents that bind salts, especially calcium, can cause the formation of the aggregate. Having made this discovery, other methods for forming the aggregate and separating the MAIF will be obvious to those skilled in the art.

EXAMPLE 3

Biological Activity Assay

The anti-inflammatory action of the MAIF was tested on edema that was caused by the injection of a solution of carrageenin into the footpads of rats. A lyophilized sample of the MAIF was dissolved in the appropriate vehicle and given intraperitoneally to experimental rats. The carrageenin was then administered to the rats in an amount of 0.1 ml of a 1% saline solution in each hind footpad. The footpads were measured before injections were given and 2.5 hours after the injections, using a thickness gauge. The results are illustrated in Tables 2 and 3.

The non-aggregated form of MAIF (peak 2 from the G-10 column) from control and hyperimmune milk caused reduction in inflammation of the rat paw at doses between 1 mg and 0.25 mg (Table 2). Both the hyperimmune milk and the regular milk exhibited activity; however, the hyperimmune material was more potent. We concluded from this that the MAIF occurs in greater concentration in the milk from hyperimmune cows.

The second peak from the DEAE column exhibited activity when isolated from either hyperimmune milk or regular milk. The activity is substantially greater in the hyperimmune milk (Table 3).

The first peak from the G-10 column, which is the aggregated form of MAIF, exhibited activity in rat paw tests (Table 2). However, the aggregated is not as potent as the nonaggregated form on equal weight basis.

It is concluded from these studies that the MAIF factor occurs naturally in cows milk. Hyperimmunization of the cows causes higher concentration of MAIF in the milk. The MAIF is a small, negatively charged molecule that can be separated from the milk by a variety of methods. The MAIF factor can form large molecular weight aggregates that do not naturally occur in milk, but form during processing.

TABLE 2
EFFECT OF MILK ANTI-INFLAMMATORY FACTOR (MAIF) ON REDUCTION OF INFLAMMATION IN RATS

| MAIF DOSAGE | Foot Pad Measurements (mm) | | | % Inflammation |
|---|---|---|---|---|
| | Before Injection | 2.5 hr. After Injection | Difference | |
| Prepared From Hyperimmune Milk | | | | |
| 2.0 mg/rat | 3.43 | 5.01 | 1.58 | 46 |
| 1.0 mg/rat | 3.49 | 5.39 | 1.90 | 54 |
| 0.5 mg/rat | 3.42 | 5.51 | 2.09 | 61 |
| 0.1 mg/rat | 3.43 | 5.86 | 2.43 | 71 |
| Control/Saline | 3.43 | 5.82 | 2.39 | 70 |
| Prepared from Normal Cows Milk | | | | |
| 2.0 mg/rat | 3.30 | 5.24 | 1.94 | 59 |
| 1.0 mg/rat | 3.31 | 5.22 | 1.91 | 58 |
| 0.5 mg/rat | 3.32 | 5.33 | 2.01 | 61 |
| 0.25 mg/rat | 3.31 | 5.42 | 2.11 | 64 |

TABLE 3
COMPARISON OF SEMIPURIFIED FRACTIONS OF MAIF ON REDUCTION OF INFLAMMATION IN RATS
(Prepared From Hyperimmune and Regular Milk)

| | Foot Pad Measurements (mm) | | | % Inflammation |
|---|---|---|---|---|
| | Before Injection | 2.5 hr. After Injection | Difference | |
| DEAE Column Second Peak Hyperimmune Milk 2 mg/rat | 3.25 | 5.04 | 1.79 | 55 |
| DEAE Column Second Peak Regular Milk 2 mg/rat | 3.30 | 5.24 | 1.94 | 59 |
| G-10 Column First Peak 2 mg/rat | 3.31 | 4.98 | 1.67 | 50 |
| Control/Saline | 3.34 | 5.63 | 2.29 | 69 |

CHEMICAL ANALYSIS OF ANTI-INFLAMMATORY FACTOR

Anti-inflammatory factor samples were analyzed chemically. MAIF is not crystalline in structure, as determined by X-ray diffraction studies. MAIF preparations gave elemental analysis consistent with carbohydrate composition. The C, H, O ratios were consistent with a polymeric or oligomeric material with some carbinol groups being oxidized to carboxyl. The slight -excess of calcium equivalents over chloride ions may be accounted for in part as carboxylate salts. The remainder may be sodium or potassium salts. However, the melting behavior, or rather the non-melting behavior, was suggestive of salt-like and/or higher molecular weight compositions. The material in the present state of purity apparently contains a variable amount of salts of calcium and chloride, probably $CaCl_2$.

Neither preparation contained a significant amount of nitrogen which precludes any peptide component in its composition. Likewise, the absence of significant amounts of nitrogen can rule out the presence of amino sugars and other nitrogen-containing materials such as various complex lipids as the major component(s).

Pyrolytic mass spectra revealed significant traces of 18-carbon fatty acids. This fact, taken together with traces of N and P, suggest the presence of a complex lipid in the factor.

Infrared spectroscopy revealed absorptions consistent with carbinol and carboxylate functionalities. Ultraviolet, visible and fluorescent spectroscopy revealed no significant amount of chromophores beyond those indicated by infrared. The anti-inflammatory factor sample was essentially devoid of sulfur.

The chemical tests are consistent with an oligomeric carbohydrate, wherein the carbonyl function (aldehyde or ketone) is tied up in the subunit linkages. The oligomeric carbohydrate also contains some sidechain oxidation to carboxylate.

The MAIF preparation is substantially, but not completely pure.

Having now generally described this invention, it will become readily apparent to those skilled in the art that many changes and modifications can be made thereto without affecting the spirit or scope thereof.

What is new and claimed and intended to be covered by letters patent of the United States is:

1. An anti-inflammatory factor, in substantially pure form, produced by a process comprising:
   (i) removing the fat from milk of a milk-producing animal to produce skimmed milk;
   (ii) removing casein from said skimmed milk to produce whey;
   (iii) removing from said whey macromolecules having a molecular weight greater than about 10,000 daltons;
   (iv) fractionating the low-molecular weight product from the previous step by ion exchange chromatography;
   (v) further purifying the anti-inflammatory factor from the previous step by molecular sieve chromatography; and
   (vi) collecting said anti-inflammatory factor.

2. The anti-inflammatory factor of claim 1, wherein said milk-producing animal is a bovid.

3. The anti-inflammatory factor of claim 1, wherein said milk-producing animal is an ovid.

4. The anti-inflammatory factor of claim 1, wherein said milk-producing animal is in a hyper-immunized state.

5. The anti-inflammatory factor of claim 4 wherein said hyperimmunized state is induced by administration of a polyvalent mixture of bacterial antigens comprising: *Stapholococcus aureus; Stapholoccocus epidermidis; Streptococcus pyogenes,* A Type 1; *Streptococcus pyogenes,* A. Type 3; *Streptococcus pyogenes.* A. Type 5; *Streptococcus pyogenes,* A. Type 8; *Streptococcus pyogenes.* A. Type 12; *Streptococcus pyogenes,* A. Type 14; *Streptococcus pyogenes,* A. Type 18; *Streptococcus pyogenes.* A. Type 22; *Aerobacter aerogenes: Escherichia coli; Pseudomonas aeruginosa; Klebsiella pneumoniae; Salmonella typhimurium; Haemophilus influenzae; Streptococcus mitis: Proteus vulgaris; Shigella dysenteriae; Diplococcus pneumoniae: Proprionibacter acnes, Actinomyces* (anaerobe); *Streptococcus mutans; Streptococcus sanguis. Streptococcus salivarius* and *Streptococcus agalactiae.*

6. The anti-inflammatory factor of claim 5, wherein said polyvalent bacterial antigen is administered to said animal orally.

7. The anti-inflammatory factor of claim 5, wherein said polyvalent vaccine is administered parenterally.

8. The anti-inflammatory factor of claim 1, wherein removal of said macromolecules of molecular weight greater than 10,000 daltons is by ultrafiltration of said whey through a molecular sieve membrane that retains molecules of 10,000 daltons.

9. The anti-inflammatory factor of claim 1, wherein said macromolecules of molecular weight greater than 10,000 daltons are removed by molecular sieve chromatography.

10. The anti-inflammatory factor of claim 1, wherein said factor has a relative molecular weight between 0 and 10,000 daltons.

11. A method of isolating a substantially pure anti-inflammatory factor from milk comprising:
 (i) removing fat from the milk of a milk producing animal to produce skimmed milk;
 (ii) removing casein from said skimmed milk to produce whey;
 (iii) removing from said whey macromolecules of molecular weight greater than 10,000 daltons; and
 (iv) fractionating the low molecular weight product from the previous step by ion exchange chromatography;
 (v) further purifying the anti-inflammatory factor from the previous step by molecular sieve chromatography; and
 (vi) collecting said anti-inflammatory factor.

12. The method of claim 11, wherein said milk-producing animal is in a hyperimmunized state.

13. The method of claim 12 wherein said hyperimmunized state is produced by administration of a mixture of bacterial antigens comprising: *Stapholococcus aureus; Stapholoccocus epidermidis: Streptococcus pyogenes,* A Type 1; *Streptococcus pyogenes,* A. Type 3; *Streptococcus pyogenes,* A. Type 5; *Streptococcus pyogenes.* A. Type 8; *Streptococcus pyogenes.* A. Type 12; *Streptococcus pyogenes,* A. Type 14; *Streptococcus pyogenes,* A. Type 18; *Streptococcus pyogenes.* A. Type 22; *Aerobacter aerogenes: Escherichia coli; Pseudomonas aeruginosa; Klebsiella pneumoniae: Salmonella typhimurium: Haemophilus influenzae; Streptococcus mitis; Proteus vulgaris; Shigella dysenteriae: Diplococcus pneumoniae: Proprionibacter acnes, Actinomyces* (anaerobe); *Streptococcus mutans; Streptococcus sanguis, Streptococcus salivarius* and *Streptococcus agalactiae.*

14. The method of claim 13, wherein said mixture of bacterial antigens is administered to said animal orally.

15. The method of claim 13, wherein said mixture of bacterial antigens is administered parenterally.

16. The method of claim 11, wherein removal of said macromolecules of molecular weight greater than 10,000 daltons comprises ultrafiltration through a molecular sieve membrane that retains molecules of greater than 10,000 daltons.

17. The method of claim 11, wherein said macromolecules of greater than 10,000 daltons are removed by molecular sieve chromatography.

18. Substantially pure anti-inflammatory factor from milk (MAIF) comprising an oligomeric carbohydrate.

19. The anti-inflammatory factor of claim 18, wherein the carbonyl function of said carbohydrate is tied up in subunit linkages.

20. The anti-inflammatory factor of claim 18, wherein said carbohydrate contains side chain carboxylate ions.

21. A method of treating inflammation in an animal which comprises administering to said animal an anti-inflammatorily effective amount of the anti-inflammatory factor of claim 1.

22. A method of treating inflammation in an animal which comprises administering to said animal an anti-inflammatorily effective amount of the anti-inflammatory factor of claim 18.

23. The method of claim 21, wherein said inflammation is caused by a condition selected from a group consisting of acute and subacute bursitis, acute nonspecific tendonitis, systemic lupus erythematosis, systemic dermatomyositis, acute rheumatic carditis, pemphigus, bullous dermatitis, herpeteformis, severe erythema, multiform exfoliative dermatitis, cirrhosis, seasonal perennial rhinitis, bronchial asthma, ectopic dermatitis, serum sickness, keratitis, opthalmicus iritis, diffuse ureitis, choriditis, optic neuritis, sympathetic opthalmia, symptomatic sarcoidosis, Loeffler's syndrome, berylliosis, and hemolytic anemia and mastitis.

* * * * *